US008118798B1

(12) United States Patent
Campbell

(10) Patent No.: US 8,118,798 B1
(45) Date of Patent: Feb. 21, 2012

(54) ABSORBENT UNDERGARMENT LINER

(76) Inventor: Antonio Montgomery Campbell, Stone Mountain, GA (US)

( * ) Notice: Subject to any disclaimer, the term of this patent is extended or adjusted under 35 U.S.C. 154(b) by 837 days.

(21) Appl. No.: 12/070,477

(22) Filed: Feb. 19, 2008

Related U.S. Application Data

(60) Provisional application No. 60/972,665, filed on Sep. 14, 2007.

(51) Int. Cl.
*A61F 13/15* (2006.01)

(52) U.S. Cl. .... 604/349; 604/353; 604/354; 604/385.04

(58) Field of Classification Search .......... 604/346–356, 604/385.04
See application file for complete search history.

(56) References Cited

U.S. PATENT DOCUMENTS

| | | | | |
|---|---|---|---|---|
| 2,976,869 A | * | 3/1961 | Silverstone et al. | 604/353 |
| 3,030,958 A | * | 4/1962 | Levin | 604/347 |
| 3,094,990 A | * | 6/1963 | Neilson | 2/400 |
| 6,565,548 B1 | * | 5/2003 | Glaug et al. | 604/385.03 |
| 7,591,811 B2 | * | 9/2009 | Crislip Wilkinson | 604/385.25 |
| 2005/0256473 A1 | * | 11/2005 | Feldkamp et al. | 604/378 |

* cited by examiner

*Primary Examiner* — Lynne Anderson
(74) *Attorney, Agent, or Firm* — Robert Z. Evora

(57) ABSTRACT

An absorbent undergarment liner including an absorbent material placed in a medial crotch area of an undergarment that is used to prevent leakage of male genitalia onto the undergarment. The absorbent undergarment liner is constructed with a lower outward flared base in which a first lower flare extends radially inward around an inner thigh region of a trunk leg toward the rear of the undergarment. A second lower flare extends radially outward toward an outer thigh region of the trunk leg. A vertical elongated portion extends upwardly and offset from the center of the open fly region of the undergarment from a front panel lower crotch region to a front panel medial region of the undergarment.

17 Claims, 5 Drawing Sheets

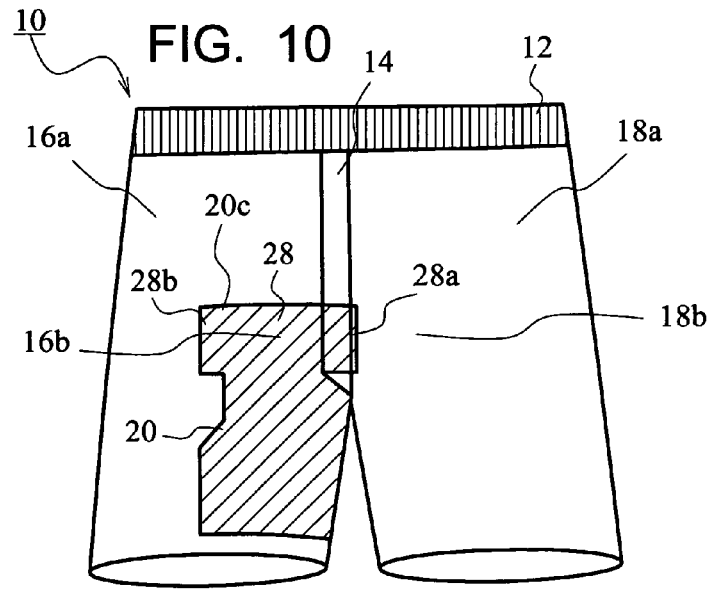
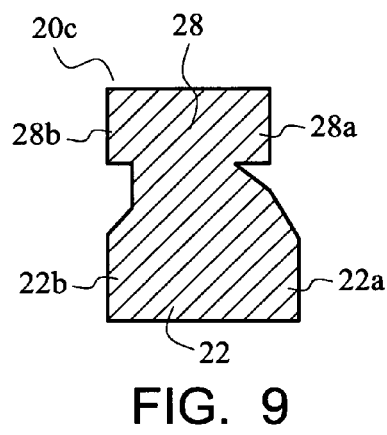
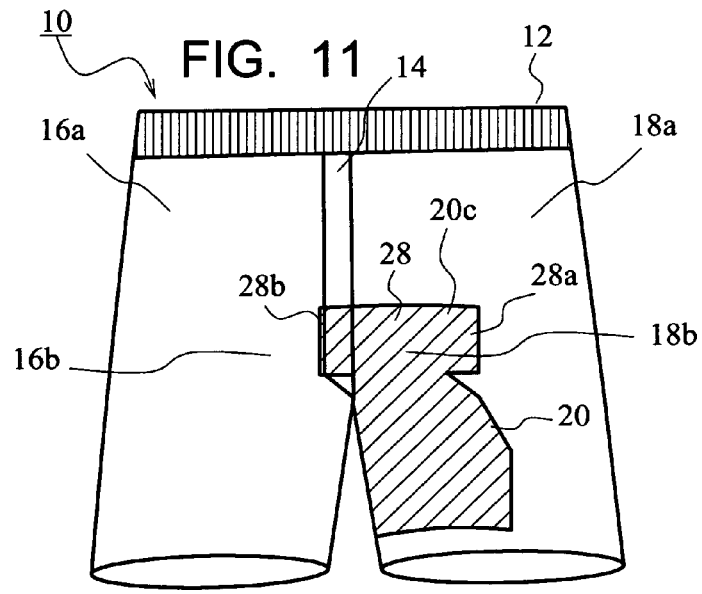

FIG. 17
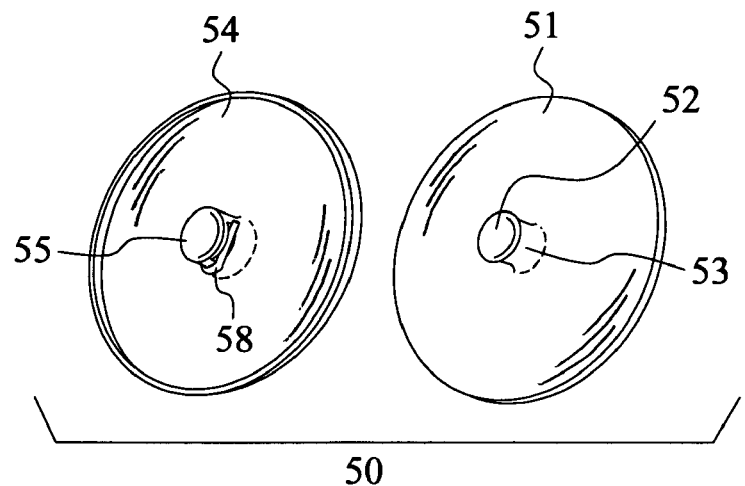
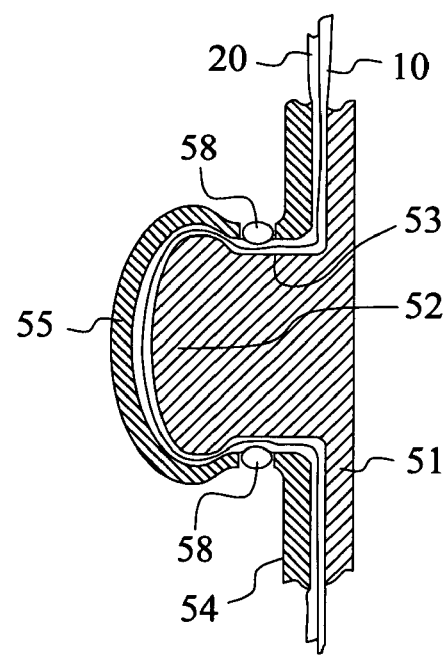
FIG. 18

ABSORBENT UNDERGARMENT LINER

CROSS REFERENCE TO RELATED APPLICATION

This application is a Non-Provisional Application which claims the benefit of the filing date of U.S. Provisional Application Ser. No. 60/972,665, entitled "Male Undergarment Liner" filed Sep. 14, 2007, the entirety of which is incorporated herein by reference.

BACKGROUND OF THE INVENTION

1. Field of the Invention

This invention relates to a sanitary undergarment liner, and in particular for absorption of leakage of bodily fluids in a torso region adjacent to the user's underwear located in and around a user's thighs.

2. Description of the Related Art

For a variety of different reasons, men frequently have unexpected seepage or drainage from their genitalia. For example, after using a restroom, a man may have additional dripping onto their undergarments. Unfortunately, the urine or other discharge tends to soil through the underwear and onto the outer garment rendering embarrassing wet spots to the outside of the trouser. Likewise, an odor from the uric acid may also penetrate through the underwear and the fabric of the outer trouser emitting a foul odor.

While sanitary pad solutions for controlling the fluid discharge of women, and bulky geriatric products for men and women are well know, never before has an inconspicuous undergarment liner solution for male seepage been proposed capable of providing the needed sense of leakage security for a man during these embarrassing situations.

Absorbent articles such as sanitary napkins, panty-liners, and incontinence pads are devices that are typically worn in the lower crotch region of underwear and are not adaptable for the zipper crotch region without causing obvious bulkiness. Although, these devices are designed to absorb and retain liquid and other discharges from the human body and to prevent body and clothing soiling, these devices are not comfortable, practical and/or inconspicuous. Sanitary napkins are a type of absorbent article worn by women with their underwear that is normally positioned between the wearer's legs; they are typically used in the perineal area of the body and are not adapted for seepage from a male organ.

Thus, there is still a longstanding need to solve this problem. In accordance with this invention, an exemplary undergarment liner is described and shown below to remedy this difficulty.

SUMMARY OF THE INVENTION

The present invention addresses the shortcomings identified in providing a hygienic, thin and highly absorbent undergarment liner that is comfortable, unnoticeable, and appropriate for use by adult and adolescent men. The absorbent undergarment liner is meant to provide coverage to the wearer's undergarment to prevent leakage or soiling from male genitalia onto the undergarment.

An object of this invention is to provide an absorbent undergarment liner including an absorbent material that, in use, is located in a medial crotch area of an undergarment. The absorbent undergarment liner is used to prevent leakage of male genitalia onto the undergarment.

According to an aspect of this invention, the undergarment liner includes a lower outward flared base in which a first lower flare extends radially inward around an inner thigh region of a trunk leg toward the rear of the undergarment. A second lower flare extends radially outward toward an outer thigh region of the trunk leg. A vertical elongated portion extends upwardly and offset from the center of the open fly region of the undergarment from a front panel lower crotch region to a front panel medial region of the undergarment.

According to yet another aspect of this invention, the undergarment may be an absorbent liner placed in an open fly region of a lower torso garment.

The absorbent liner may be constructed to include an absorbent layer, a liquid impermeable layer, an adhesive layer and a particle protectant layer. The liquid impermeable layer may be disposed to prevent liquid from penetrating from the absorbent layer toward the lower torso garment. The adhesive layer may be disposed adjacent to the liquid impermeable layer to attach the absorbent liner to a region inside of the crotch area of a lower torso garment. And, the particle-protectant layer may be provided to protect the adhesive layer from contacting particles prior to adhering the absorbent liner to the lower torso garment.

These and other objects, features, and/or advantages may accrue from various aspects of embodiments of the present invention, as described in more detail below.

BRIEF DESCRIPTION OF THE DRAWINGS

Various exemplary embodiments of this invention will be described in detail, wherein like reference numerals refer to identical or similar components or steps, with reference to the following figures, wherein:

FIG. 9 depicts yet another exemplary alternate construction of the undergarment liner according to this invention.

FIG. 10 illustrates a front view of the alternate undergarment with the undergarment liner disposed on the left trunk leg in accordance with this invention.

FIG. 11 illustrates a front view of the alternate undergarment with the undergarment liner disposed on the right trunk leg in accordance with this invention.

FIG. 17 depicts an exemplary fastening mechanism according to this invention.

FIG. 18 depicts an exemplary fastening mechanism securing an undergarment liner to an undergarment according to this invention.

DETAILED DESCRIPTION OF EXEMPLARY EMBODIMENTS

Particular embodiments of the present invention will now be described in greater detail with reference to the figures.

Figure 1:
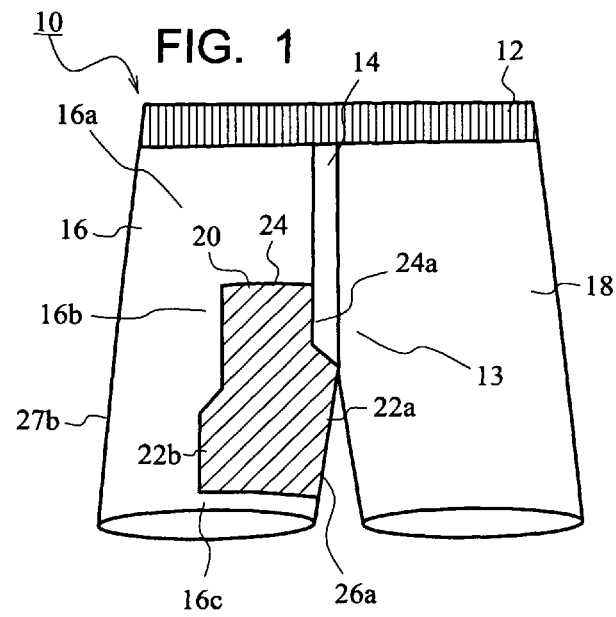
FIG. 1 illustrates a front view of the undergarment including an undergarment liner disposed on the left trunk leg in accordance with this invention.

FIG. 1 illustrates a front view of the undergarment 10. Although shown as boxer briefs, the undergarment may be any type of undergarment, including but not limited to, briefs, bikini style bottoms and/or any other type of undergarment or bottoms worn by a wearer in accordance with this invention.

Figure 2:
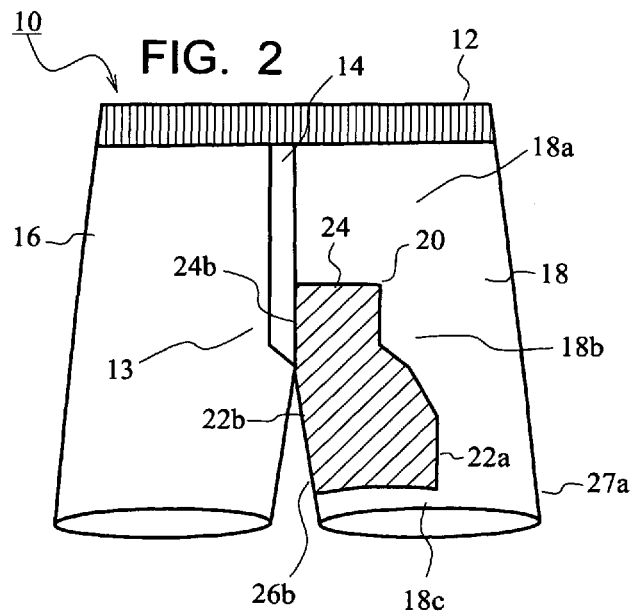
FIG. 2 illustrates a front view of the undergarment including the undergarment liner disposed on the right trunk leg in accordance with this invention.

Referring to FIGS. 1-2 in more detail, the undergarment 10 includes an elastic band 12, a left trunk leg 16, a right trunk leg 18 and an overlapping open fly 14 disposed in a zipper region between the left trunk leg 16 and the right trunk leg 18.

FIG. 1 shows the left trunk leg 16 including a left side front panel 16a including a medial region 16b and a lower leg region 16c. Likewise, FIG. 2 depicts the right trunk leg 18 including a right side front panel 18a including a medial region 18b and a lower leg region 18c.

The open fly 14 is disposed in the zipper region and is adapted to allow the male genitalia to be extracted without removing or pulling down the undergarment 10. The undergarment 10 may be secured shut by various methods for closing the open fly 14 portion, including but not limited to: snaps, a zipper, a button or two and/or any other method for closing the gaping opening in the open fly 14. Many undergarments constructed do not need a fastening mechanism to close up the open fly area because the fabric at the open fly 14 is designed to sufficiently overlap and fully cover the opening.

The traditional boxer undergarment 10 construction includes a "balloon seat." That is, the undergarment 10 includes a generous panel of loosely-fitting fabric in the center rear to accommodate the wearer's various movements, such as bending forward, sideways and the like. Conventional sewing design of boxer undergarments are made with a panel seat including two seams running on the outer edges of the back seating area, thereby creating a center rear panel that does not easily get wedged within the buttocks of the wearer.

As is conventionally known, the undergarment 10 may be constructed from one or more various suitable materials, including but not limited to: cotton, Nylon, SPANDEX, and/or the like. It is to be also understood that undergarments are usually sewn together by stitching, however, for clarity purposes, the drawings may not show typical stitching or other type of fastening means, but it is to be understood as being inherent in the design of the undergarment 10.

Figure 3:
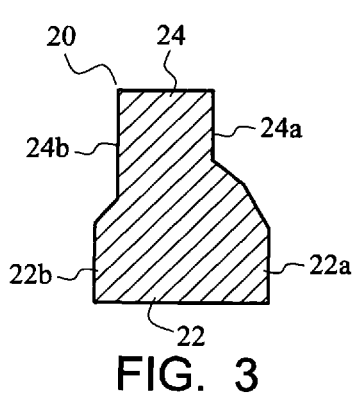
FIG. 3 depicts a plan view illustration of the undergarment liner according to this invention.

FIGS. 1-3 depict an exemplary illustration of an undergarment liner 20. As shown, at least one undergarment liner 20 is placed within a crotch area 13 of the undergarment 10. As shown in FIG. 3, the undergarment liner 20 is constructed of a lower outward flared base 22 and a vertical elongated portion 24 that extends upward from the lower leg region 16c to the medial region 16b of the garment 10. The foot print of the undergarment liner 20 is constructed to substantially cover the crotch area 13 so that any leakage from the male genitalia can be captured by an absorbent material integrated into the undergarment liner 20. This use and positioning is different from the use and positioning of a feminine liner which is concerned with absorbing fluids from the female genitalia in an internal crotch area defined in the lowermost crotch panty area between the legs and the buttocks of the user.

According to this invention, the garment liner 20 may be positioned anywhere in the crotch region, as defined above, within an undergarment, and/or on the lower torso garment itself as will be described lower. Although the undergarment liner 20 is shown and described for use on the inside of an undergarment 10, it is to be understood that the undergarment liner 20 may also on the outside of the undergarment 10 and/or applied directly a pair of trousers pants or shorts. That is, the undergarment liner 20 may be attached directly to the inside of the trousers pants or shorts with, or without, the use of an undergarment 10.

In describing the "crotch area" and the placement of the undergarment liner 20, it is important to note that the undergarment liner 20 of this invention is to be positioned higher up in the crotch area which is adjacent to a region where a zipper on a pair of trousers or shorts would normally be located. This location is, in alignment with the end of a male organ which is where leakage or seepage there from would normally occur. This position is different, and not to be confused with, the perineal position (i.e., the area between the anus and the genitals) in which a female sanitary napkin would normally be used.

FIGS. 1 and 2 demonstrate the preferred placement for the undergarment liner 20 of this invention. FIG. 1 depicts use of the undergarment liner 20 on a left side panel 16d of a left trunk leg 16. In FIG. 1, the undergarment liner 20 is positioned in the crotch area 13 adjacent to the lowermost end of the open fly 14.

A first lower flare 22a extends radially inward around an inner thigh 26a region of the left trunk leg 16 toward the rear of the undergarment 10. A second lower flare 22b extends radially outward toward an outer thigh 27a region of the left trunk leg 16. The right edge 24a of the vertical elongated portion 24 is disposed adjacent to the open fly 14 and extends upward from the lower leg region 16c to medial region 16b of the undergarment 10. It is to be understood that the vertical elongated portion 24 may extend as far as to the waistband 12.

FIG. 2 illustrates use of the undergarment liner 20 on a right side panel 18a of a right trunk leg 18. As shown, the undergarment liner 20 is disposed in the crotch area 13 on the right trunk leg 18. The undergarment liner 20 is positioned adjacent to the lowermost end of the open fly 14. The second lower flare 22b extends radially inwardly around an inner thigh 26b region of the right trunk leg 18 toward the rear of the undergarment 10. The first lower flare 22a extends radially outwardly toward an outer thigh 27b region of the right trunk leg 18. In position, a left edge 24b of the vertical elongated portion 24 is disposed adjacent to the open fly 14 and extends upward from the lower leg region 18c to medial region 18b of the right trunk leg 18 of the undergarment 10.

Figure 4:
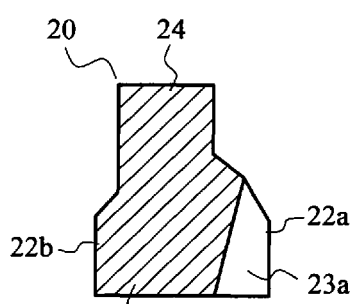
FIG. 4 depicts a plan view of the undergarment liner adapted for use on the left trunk leg of the undergarment according to this invention.
Figure 5:
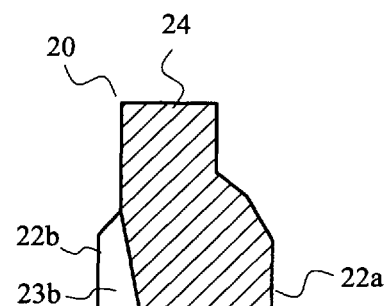
FIG. 5 depicts a plan view of the undergarment liner adapted for use on the right trunk leg of the undergarment according to this invention.

As shown in FIGS. 4 and 5, regions 23a, 23b on undergarment liner 20 may be used as an adhesive and/or other location suitable for providing an attachment mechanism. For purposes of this exemplary embodiment, regions 23a, 23b will be described as adhesive 23a, 23b. The adhesive 23a, 23b is shown disposed on the first lower flare 22a and the second lower flare 22b, respectively. However, it is to be understood that the adhesive 23a, 23b (or attachment mechanism) may be disposed on any portion of the undergarment liner 20. Various types of adhesives devices and/or attachment mechanisms may be used in accordance with this invention, including but not limited to glue, snaps, Velcro, static adhesion, and the like.

Figure 6:
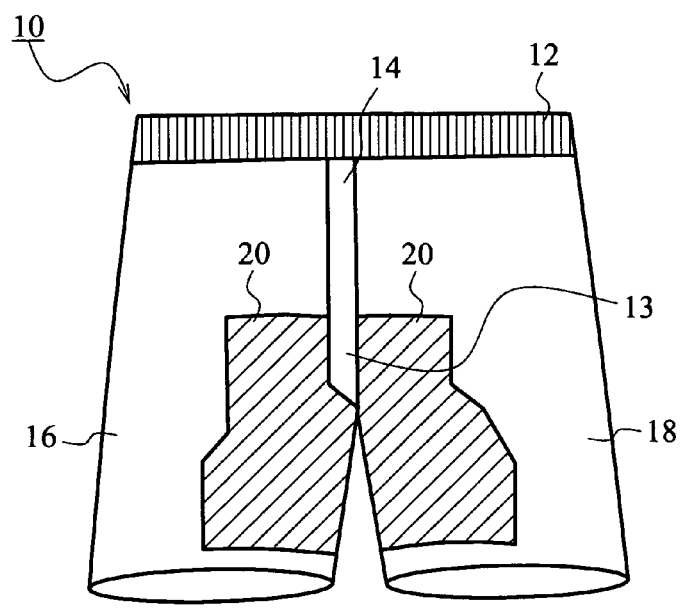
FIG. 6 illustrates a front view of the undergarment including a pair of undergarment liners disposed on the right and left trunk legs in accordance with this invention.

FIG. 6 demonstrates the flexibility of the use of the undergarment liner 20. As shown, two undergarment liners 20 may be positioned on the undergarment 10 in a side-by-side arrangement. That is, one undergarment liner 20 may be placed on the left trunk leg 16 and another undergarment liner 20 may be placed on the right trunk leg 18 located adjacent thereto. As shown by this configuration, substantial coverage is provided to the wearer in the crotch area 13.

Figure 7:
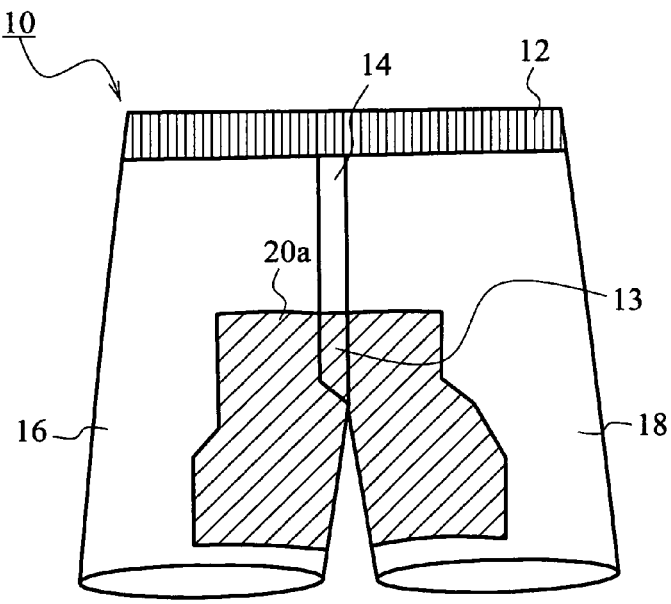
FIG. 7 illustrates a front view of another exemplary contiguous undergarment liner that spans across the right and left trunk legs and the crotch area in accordance with this invention.
Figure 12:
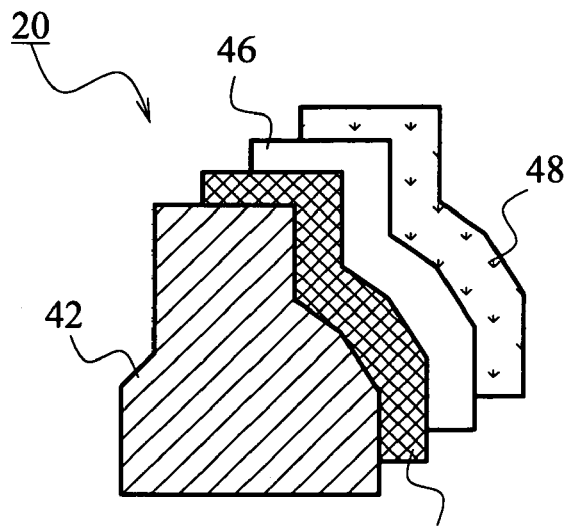
FIG. 12 depicts an exemplary construction of the undergarment liner including at least four layers according to this invention.

FIG. 7 shows an alternative embodiment in which another exemplary undergarment liner 20a may be constructed as a single contiguous liner that provides more coverage that the two undergarment liners 20 as shown in FIG. 6 disposed side-by-side. The contiguous undergarment liner 20a provides maximum coverage to the wearer in that it also provides coverage over the open fly 14 area.

It is another aspect of this invention to construct the undergarment liner to include a scented or unscented deodorant to assist in masking any unpleasant order from emanating from with the crotch area 13. In general, an object of the invention is to provide an absorbent solution to the leakage and/or seepage of the fluids from the male organ. In accordance with this invention, it is to be understood that the garment liner 20 may flexibly be designed of various sizes, shapes, layers, colors and/or materials from which a user may select. By way of example of the flexibility in the design and construction of the undergarment liner according to this invention, another exemplary illustration of the undergarment liner is depicted in FIG. 8.

Figure 8:
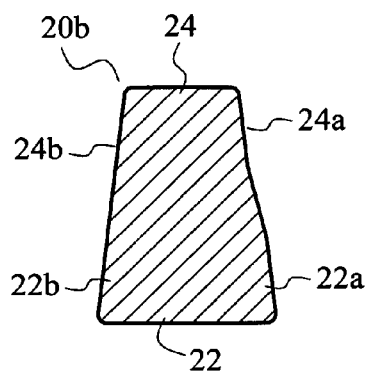
FIG. 8 depicts an alternate simple construction for the undergarment liner according to this invention.

FIG. 8 depicts an undergarment liner 20b that is shown simpler in design. The undergarment liner 20a may be utilized similar in use and construction to the undergarment liners 20, 20a described above in FIGS. 1-7. In particular, the undergarment liner 20b includes a first lower flare 22a that is used to extend radially inward around an inner thigh 26a region of the left trunk leg 16 toward the rear of the undergarment 10. Likewise, a second lower flare 22b is designed to extend radially outward toward an outer thigh 27a region of the left trunk leg 16. The right edge 24a of the vertical elongated portion 24 may be disposed adjacent to the open fly 14 and extends upward from the lower leg region 16c to medial region 16b of the undergarment 10.

FIGS. 9-11 depict yet another exemplary embodiment in which the undergarment liner 20c includes an upper flared portion 28. As shown in FIG. 9, the upper flared portion 28 includes a left upper flare 28a and a right upper flare 28b.

FIG. 10 illustrates the undergarment liner 20c disposed on the left side panel 16a of the undergarment 10. The right upper flared portion 28a extends radially inward across the left side medial region 16b toward a right side medial region 18b. The right upper flared portion 28a extends over the open fly 14 region of the undergarment 10 where a left side front panel 16a and a right side front panel 18a intersect at the open fly 14. This right upper flared portion 28a provides additional coverage from leakage and soiling across the area defined by the open fly 14.

FIG. 11 depicts a mirrored application in which the undergarment liner 20c is shown on the right side panel 18a of the undergarment 10. The left upper flared portion 28b extends radially inward across the right side medial 18b region toward a left side medial region 16b. Likewise, the left upper flared portion 28b extends over the open fly 10 region of the undergarment 10 where the left side front panel 16a and a right side front panel 18a intersect to provide additional coverage from leakage and soiling across the open fly 14 area.

FIGS. 12-16 illustrate an exemplary construction for the undergarment liner 20 (and/or any of the other exemplary undergarment liners described herein). As shown, the undergarment liner 20 is composed of at least four layers 42, 44, 46, 48.

Figure 13:
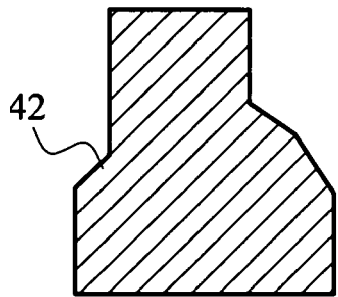
FIG. 13 illustrates an absorbent layer constructed as part of the undergarment liner according to this invention.

FIG. 13 illustrates an absorbent layer 42 constructed as part of the undergarment liner 20 which includes an absorbent material. The absorbent material used in the absorbent layer 42 may be composed from any known material, such as an absorbent material used in other commercially available product, such as those produced by KOTEX, STAYFREE, DEPEND, etc., and/or any other type of suitable pad typically used for incontinence pads and the like.

Figure 14:
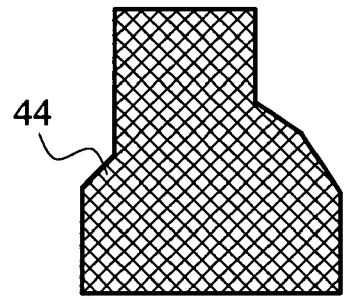
FIG. 14 depicts a leak-proof layer constructed as part of the undergarment liner according to this invention.

FIG. 14 depicts a leak-proof layer 44 constructed as part of the undergarment liner 20. The leak-proof layer 44 attached to the absorbent layer 42 may be composed from any known waterproof material, such as a polymer, nylon, a metallic, and/or any other suitable fluid impermeable material.

Figure 15:
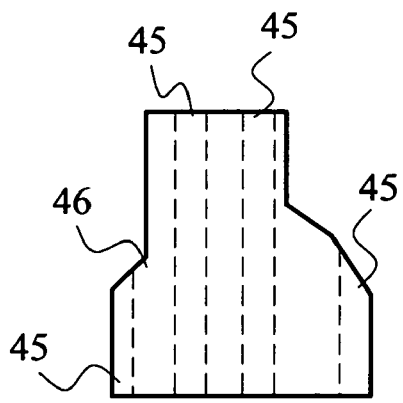
FIG. 15 shows an adhesive layer constructed as part of the undergarment liner according to this invention.

FIG. 15 shows an adhesive layer 46 constructed as part of the undergarment liner 20. The adhesive layer 46 is attached to the leak-proof layer 44. The adhesive layer 46 may be composed from any known adhesive material, such as glue, Velcro and/or any other suitable adhesive material. Although the entire adhesive layer 46 is shown covered with the adhesive, it is to be understood that the adhesive material may be applied to the leak-proof layer 44 as adhesive strips 45 as shown in hidden lines. In the alternative to an adhesive, the attachment means may be any type of commercially available attachment mechanism, including but not limited to, a snap, Velcro and the like.

Figure 16:
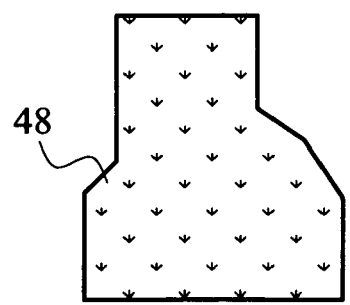
FIG. 16 shows a particle-protectant layer constructed as part of the undergarment liner according to this invention.

FIG. 16 shows a particle-protectant layer 48 constructed as part of the undergarment liner 20. The particle-protectant layer 48 lies adjacent to the adhesive layer 46 and serves to cover and protect the adhesive layer 46 from collecting dust and particle debris. The particle-protectant layer 48 may be made from any known protectant material, such as a grease paper, a wax paper, and/or any other suitable material having properties conducive to being easily removed from an adhesive without removing the adhesive.

It can now be seen that the combination of the various layers 42, 44, 46, 48, and/or any other suitable combination of layered materials may be used to form the undergarment liner 20. The various layers 42, 44, 46 may be fixedly attached to each other in a variety of different ways, such as by stitching, gluing, welding and/or any other suitable manner commonly known for fastening various panel layers to each other.

When the undergarment liner 20 is ready for use, the particle-protectant layer 48 may be peeled off of the adjacent adhesive layer 46 exposing the adhesive layer 46 for use. The undergarment 10 may be turned inside out and the undergarment liner 20 may be positioned onto the inside of the undergarment 10 between the wearer and the undergarment 10 so that the undergarment 10 is also protected from soiling. The undergarment liner 20 may then be positioned and secured by the adhesive 12 on the left trunk leg 16 as shown in FIG. 1, or secured by the adhesive on the right trunk leg 18 as shown in FIG. 2.

As mentioned previously, the attachment means may be any type of commercially available attachment mechanism. By way of illustration, FIG. 17 shows a snap fastener 50 that may be employed as the fastening mechanism in accordance with this invention. The snap fastener 50 includes a first clip portion 51 and a second receiving clip portion 54. The first clip portion 51 includes a male protruding portion 52 that is received by a retainer portion 55 in the second receiving clip portion 54. As shown in FIG. 18, the end of the male protruding portion 52 is enlarged and captivated by a retaining clip 58.

FIG. 18 depicts the operation of the snap fastener 50. In use, the undergarment liner 20 and the undergarment 10 are secured to each other when the male protruding portion 52 of the first clip portion 51 urges a portion of the undergarment liner 20 and the undergarment 10 into the retainer portion 55 in the second receiving clip portion 54. The male protruding portion 52 is compressed until a neck 53 in the enlarged head of the male protruding portion 52 is secured by the retaining clip 58, thereby preventing the male protruding portion 52 from easily slipping out without substantial force applied to overcome the resilient properties of the retaining clip 58 clasping the neck 53 of the male protruding portion 52.

After use, the undergarment liner 20 may be removed from the undergarment 10 simply by pulling the releasing the first clip portion 51 from within the second receiving clip portion 54 with substantial force to overcome the resilient properties of the retaining clip 58. Although the fastening mechanism shown is the snap fastener 50 described above, any number of commercially available fastening mechanisms may be used to secure the undergarment liner 20 to the undergarment 10 and/or any other suitable material.

A variety of unique other uses are contemplated in accordance with this invention. For example, when a quilt is worn, it is customary not to wear an undergarment, the undergarment liner 20 then can be used as a lower torso garment liner to prevent leakage and/or seepage of fluid from a male genitalia. Since the liner according to this invention is intended to be soft, another advantage is apparent where undergarment may not be worn, perhaps because an undergarment may be uncomfortable or for any other medicinal or non-medicinal reason, and the male genitalia will be protected from the potentially more rugged from material of the lower torso garment. Lower torso garment may be many, including but not limited to, a pair of pants, a pair of shorts, a skirt such as a Scottish quilt and/or a dress or the like.

It will be recognized by those skilled in the art that changes or modifications may be made to the above described embodiments without departing from the broad inventive concepts of the invention. It is understood therefore that the invention is not limited to the particular embodiments which are described, but is intended to cover all modifications and changes within the scope and spirit of the invention.

What is claimed is:

1. An undergarment liner, comprising:
an absorbent material constructed to substantially cover the surface area of the undergarment liner, the undergarment liner being located within a crotch area of an undergarment and being asymmetrically attached offset from a center axis of the undergarment,
wherein the undergarment liner is constructed to include:
a lower outward flared base located on a front panel lower crotch region of the undergarment, and
a vertical elongated portion having an inner edge that extends upwardly, offset from, and adjacent to the center of the undergarment from the front panel lower crotch region to at least a front panel medial region of the undergarment.

2. The undergarment liner recited in claim 1, wherein the undergarment liner is positioned adjacent to the lowermost end of an open fly, the lower outward flared base includes:
a first lower flare that extends radially inward around an inner thigh region of a trunk leg toward the rear of the undergarment; and
a second lower flare that extends radially outward toward an outer thigh region of the trunk leg.

3. The undergarment liner recited in claim 1, wherein an inner edge of the vertical elongated portion extends adjacent to the open fly of the undergarment.

4. The undergarment liner recited in claim 1, further includes an upper flared portion that is positioned in the medial region at the center of the undergarment where a left side front panel and a right side front panel intersect.

5. The undergarment liner recited in claim 4, wherein the upper flared portion extends radially inward across the medial region of the undergarment where a left side front panel and a right side front panel intersect.

6. The undergarment liner recited in claim 1, wherein the layout of the undergarment liner is constructed to cover the span of a leakage area caused by male genitalia.

7. The undergarment liner recited in claim 1, wherein the undergarment liner is secured to the crotch area of the undergarment with a fastening mechanism selected from at least one of an: adhesive, a clip, a snap and hook and loop fastener.

8. The undergarment liner recited in claim 7, wherein the snap comprises:
a first clip portion including a protruding portion and a second retainer portion including a receiving hole,
wherein the undergarment liner and the undergarment are secured to each other when the protruding portion urges and wedges a piece of the undergarment liner and the undergarment through the receiving hole in the second retainer portion.

9. An absorbent undergarment liner, comprising:
an absorbent layer including an absorbent pad that substantially spans across the surface area of the absorbent undergarment liner; and
an adhesive layer including an adhesive that substantially spans across the surface area of the absorbent undergarment liner, and adapted to attach the absorbent undergarment liner to a region inside of the crotch area of an undergarment, and being asymmetrically attached offset from a center axis of the undergarment so that the absorbent undergarment liner is positioned to absorb and protect the undergarment against leakage from male genetalia, and
wherein the absorbent undergarment liner extends adjacent to, and from the center axis of the undergarment across a front medial surface of the undergarment.

10. The absorbent undergarment liner recited in claim 9, further including a liquid impermeable layer disposed between the absorbent layer and the adhesive layer to prevent liquid from penetrating from the absorbent layer to the undergarment.

11. The absorbent undergarment liner recited in claim 9, further including a particle-protectant layer disposed on adhesive layer that protects the adhesive layer from contacting particles prior to adhering the absorbent undergarment liner to the undergarment.

12. An absorbent liner, comprising:
an absorbent material constructed to substantially cover the surface area of the absorbent liner, the absorbent liner being located within a crotch area of an undergarment and being asymmetrically attached offset from a center axis of an open fly region of a lower torso garment,
wherein the absorbent liner is constructed to include:
a lower outward flared base positioned at a front panel lower crotch region of the lower torso garment, and
a vertical elongated portion having an inner edge that extends upwardly, offset from, and adjacent to the center axis of the lower torso garment from the front panel lower crotch region to at least a front panel medial region of the lower torso garment.

13. The absorbent liner recited in claim 12, wherein the absorbent liner is positioned adjacent to the lowermost end of the open fly region, the lower outward flared base includes:
   a first lower flare that extends radially inward around an inner thigh region of a trunk leg toward the rear buttocks region of the lower torso garment; and
   a second lower flare that extends radially outward toward an outer thigh region of the trunk leg of the lower torso garment.

14. The absorbent liner recited in claim 12, wherein an inner edge of the vertical elongated portion extends adjacent to the open fly region of the lower torso garment.

15. The absorbent liner recited in claim 12, further includes an upper flared portion that is positioned in the medial region at the center of the lower torso garment where a left side front panel and a right side front panel of the lower torso garment intersect.

16. The absorbent liner recited in claim 12, further comprising:
   an absorbent layer;
   a liquid impermeable layer disposed adjacent to the absorbent layer to prevent liquid from penetrating from the absorbent layer toward the lower torso garment;
   an adhesive layer disposed adjacent to the liquid impermeable layer to attach the absorbent liner to a region inside of the crotch area of an lower torso garment; and
   a particle-protectant layer disposed on adhesive layer to protect the adhesive layer from contacting particles prior to adhering the absorbent liner to the lower torso garment.

17. The absorbent liner recited in claim 12, wherein the open fly region of the lower torso garment is a zipper region in an article of clothing selected from at least one of: a pair of pants, a pair of shorts, a skirt and a dress.

* * * * *